US012064158B2

(12) United States Patent
Marinkovich

(10) Patent No.: US 12,064,158 B2
(45) Date of Patent: Aug. 20, 2024

(54) ORTHOPEDIC IMPACTOR TOOL

(71) Applicant: Zimmer, Inc., Warsaw, IN (US)

(72) Inventor: Dragomir Marinkovich, Hales Corners, WI (US)

(73) Assignee: Zimmer, Inc., Warsaw, IN (US)

( * ) Notice: Subject to any disclaimer, the term of this patent is extended or adjusted under 35 U.S.C. 154(b) by 380 days.

(21) Appl. No.: 17/587,866

(22) Filed: Jan. 28, 2022

(65) Prior Publication Data

US 2022/0240947 A1 Aug. 4, 2022

Related U.S. Application Data

(60) Provisional application No. 63/143,548, filed on Jan. 29, 2021.

(51) Int. Cl.
*A61B 17/92* (2006.01)
*A61B 17/16* (2006.01)

(52) U.S. Cl.
CPC .......... *A61B 17/92* (2013.01); *A61B 17/1604* (2013.01); *A61B 17/162* (2013.01);
(Continued)

(58) Field of Classification Search
CPC . A61B 17/92; A61B 17/921; A61B 2017/922; A61B 2017/924;
(Continued)

(56) References Cited

U.S. PATENT DOCUMENTS

| | | | |
|---|---|---|---|
| 974,267 | A | 11/1910 | Hennessy et al. |
| 2,542,695 | A | 2/1951 | Neff et al. |

(Continued)

FOREIGN PATENT DOCUMENTS

| | | |
|---|---|---|
| AU | 2019203142 | 11/2019 |
| AU | 2020200771 | 2/2020 |

(Continued)

OTHER PUBLICATIONS

"International Application Serial No. PCT/US2022/014380, Invitation to Pay Additional Fees mailed May 3, 2022", 5 pgs.

(Continued)

*Primary Examiner* — Eric S Gibson
(74) *Attorney, Agent, or Firm* — SCHWEGMAN LUNDBERG & WOESSNER, P.A.

(57) ABSTRACT

Disclosed herein are orthopedic impact tools and methods of use thereof. The orthopedic impact tools can include a housing, a tube assembly, a reverse impact plate, an anvil and an impact mechanism. The housing can include a hand grip portion and an impact mechanism housing portion. The tube assembly can include a first tube portion and a second tube portion. The reverse impact plate can be disposed in between the first tube portion and the second tube portion. The anvil can include a forward impact surface. The impact mechanism can include a motor, a piston, a ram, and a rotary to linear conversion mechanism drivingly connecting the motor to the piston. The piston can be disposed within the first tube portion and the ram can be disposed in the second tube portion and movable into contact between the reverse impact plate and the forward impact surface.

18 Claims, 12 Drawing Sheets

(52) U.S. Cl.
CPC .... *A61B 17/1628* (2013.01); *A61B 2017/924* (2013.01); *A61B 2017/927* (2013.01)

(58) Field of Classification Search
CPC ........ A61B 2017/925; A61B 2017/927; A61B 2017/928
See application file for complete search history.

(56) References Cited

U.S. PATENT DOCUMENTS

| | | | | |
|---|---|---|---|---|
| 3,450,215 | A | 6/1969 | Emery | |
| 3,472,323 | A | 10/1969 | Hall | |
| 3,626,935 | A | 12/1971 | Pollock et al. | |
| 3,752,161 | A | 8/1973 | Bent | |
| 4,298,074 | A | 11/1981 | Mattchen | |
| 4,466,429 | A | 8/1984 | Loscher et al. | |
| 4,651,833 | A | 3/1987 | Karpf et al. | |
| 4,834,092 | A | 5/1989 | Alexson et al. | |
| 5,057,112 | A | 10/1991 | Sherman et al. | |
| 5,108,400 | A | 4/1992 | Appel et al. | |
| 5,152,352 | A | 10/1992 | Mandanis | |
| 5,163,519 | A | 11/1992 | Mead et al. | |
| 5,210,918 | A | 5/1993 | Wozniak | |
| 5,282,805 | A | 2/1994 | Richelsoph et al. | |
| 5,352,230 | A | 10/1994 | Hood | |
| 5,353,230 | A | 10/1994 | Maejima et al. | |
| 5,431,660 | A | 7/1995 | Burke | |
| 5,485,887 | A | 1/1996 | Mandanis | |
| 5,553,675 | A | 9/1996 | Pitzen et al. | |
| 6,126,694 | A | 10/2000 | Gray, Jr. | |
| 6,159,214 | A | 12/2000 | Michelson | |
| 6,264,660 | B1 | 7/2001 | Schmidt et al. | |
| 6,264,661 | B1 | 7/2001 | Mandanis et al. | |
| 6,368,324 | B1 | 4/2002 | Dinger | |
| 6,520,266 | B2 * | 2/2003 | Bongers-Ambrosius | B25D 11/12 173/2 |
| 6,626,913 | B1 | 9/2003 | Mckinnon et al. | |
| 6,814,738 | B2 | 11/2004 | Naughton et al. | |
| 6,868,918 | B2 * | 3/2005 | Shinohara | B23Q 5/027 30/392 |
| 7,090,677 | B2 | 8/2006 | Fallin et al. | |
| 7,189,241 | B2 | 3/2007 | Yoon et al. | |
| 7,637,327 | B2 | 12/2009 | Grunig | |
| 8,002,776 | B2 | 8/2011 | Liu et al. | |
| 8,393,409 | B2 * | 3/2013 | Pedicini | B25D 11/125 173/132 |
| 8,444,647 | B2 | 5/2013 | Walen et al. | |
| 8,465,492 | B2 | 6/2013 | Estes | |
| 8,556,901 | B2 | 10/2013 | Anthony et al. | |
| 8,602,124 | B2 | 12/2013 | Pedicini | |
| 8,695,726 | B2 | 4/2014 | Pedicini | |
| 8,894,654 | B2 | 11/2014 | Anderson | |
| 8,936,105 | B2 * | 1/2015 | Pedicini | A61B 17/1628 173/132 |
| 8,936,106 | B2 * | 1/2015 | Pedicini | A61B 17/1626 173/132 |
| 9,168,154 | B2 | 10/2015 | Behzadi | |
| 9,186,158 | B2 | 11/2015 | Anthony et al. | |
| 9,198,675 | B2 | 12/2015 | Nelson et al. | |
| 9,220,612 | B2 | 12/2015 | Behzadi | |
| 9,554,965 | B2 | 1/2017 | Foehrenbach | |
| 9,629,641 | B2 | 4/2017 | Ferro | |
| 9,649,202 | B2 | 5/2017 | Behzadi et al. | |
| 9,877,734 | B2 | 1/2018 | Anderson | |
| 9,901,354 | B2 | 2/2018 | Pedicini | |
| 9,931,151 | B2 * | 4/2018 | Donald | A61B 90/30 |
| 9,943,318 | B2 | 4/2018 | Anthony et al. | |
| RE46,954 | E | 7/2018 | Pedicini | |
| 10,028,754 | B2 * | 7/2018 | Johnson | A61B 17/1659 |
| RE46,979 | E | 8/2018 | Pedicini | |
| 10,159,500 | B2 | 12/2018 | Chavarria et al. | |
| 10,172,722 | B2 | 1/2019 | Behzadi | |
| 10,245,160 | B2 | 4/2019 | Behzadi | |
| 10,245,162 | B2 | 4/2019 | Behzadi | |
| 10,251,663 | B2 | 4/2019 | Behzadi | |
| 10,299,930 | B2 | 5/2019 | Behzadi | |
| 10,342,591 | B2 | 7/2019 | Pedicini | |
| 10,368,882 | B2 | 8/2019 | Ferro et al. | |
| 10,413,425 | B2 | 9/2019 | Behzadi | |
| 10,426,540 | B2 | 10/2019 | Behzadi | |
| 10,441,244 | B2 | 10/2019 | Behzadi | |
| 10,456,271 | B2 | 10/2019 | Behzadi | |
| 10,463,505 | B2 | 11/2019 | Behzadi | |
| 10,470,897 | B2 | 11/2019 | Behzadi | |
| 10,478,318 | B2 | 11/2019 | Behzadi et al. | |
| 10,568,643 | B2 * | 2/2020 | Johnson | A61B 17/164 |
| 10,603,173 | B2 | 3/2020 | Carr et al. | |
| RE47,963 | E | 4/2020 | Pedicini | |
| 10,610,379 | B2 | 4/2020 | Behzadi | |
| RE47,997 | E | 5/2020 | Pedicini | |
| 10,653,533 | B2 | 5/2020 | Behzadi | |
| 10,660,767 | B2 | 5/2020 | Behzadi | |
| 10,729,559 | B2 | 8/2020 | Behzadi et al. | |
| RE48,184 | E | 9/2020 | Pedicini | |
| RE48,251 | E | 10/2020 | Pedicini | |
| 11,013,503 | B2 * | 5/2021 | Pedicini | A61F 2/4607 |
| 11,490,943 | B2 * | 11/2022 | Haiat | A61F 2/4607 |
| 11,918,268 | B2 * | 3/2024 | Doyle | A61B 17/92 |
| 11,925,359 | B2 | 3/2024 | Slocum et al. | |
| 2010/0137760 | A1 * | 6/2010 | Schulz | A61H 23/02 601/108 |
| 2011/0270256 | A1 | 11/2011 | Nelson et al. | |
| 2012/0172939 | A1 * | 7/2012 | Pedicini | A61B 17/1604 606/86 R |
| 2012/0215267 | A1 * | 8/2012 | Pedicini | B25D 11/125 606/86 R |
| 2012/0259339 | A1 | 10/2012 | Hood et al. | |
| 2013/0161050 | A1 * | 6/2013 | Pedicini | B25D 17/00 173/201 |
| 2013/0261681 | A1 | 10/2013 | Bittenson | |
| 2014/0318819 | A1 * | 10/2014 | Pedicini | A61B 17/1604 173/2 |
| 2014/0318823 | A1 * | 10/2014 | Pedicini | A61B 17/1628 173/201 |
| 2015/0196343 | A1 * | 7/2015 | Donald | A61B 17/92 606/100 |
| 2016/0199199 | A1 * | 7/2016 | Pedicini | A61B 17/92 606/100 |
| 2017/0020536 | A1 * | 1/2017 | Johnson | A61B 17/92 |
| 2018/0055518 | A1 | 3/2018 | Pedicini | |
| 2018/0055552 | A1 | 3/2018 | Pedicini | |
| 2018/0318089 | A1 | 11/2018 | Carr et al. | |
| 2018/0360464 | A1 | 12/2018 | Irvine | |
| 2019/0167434 | A1 | 6/2019 | Satterthwaite et al. | |
| 2019/0183554 | A1 | 6/2019 | Pedicini | |
| 2019/0247057 | A1 | 8/2019 | Anderson | |
| 2019/0282286 | A1 | 9/2019 | Pedicini | |
| 2022/0142693 | A1 | 5/2022 | Slocum | |
| 2022/0226033 | A1 | 7/2022 | Slocum et al. | |
| 2022/0240946 | A1 | 8/2022 | Slocum et al. | |
| 2022/0240947 | A1 * | 8/2022 | Marinkovich | A61B 17/162 |
| 2022/0240998 | A1 | 8/2022 | Slocum | |
| 2022/0273317 | A1 * | 9/2022 | Levy | A61B 17/1624 |
| 2023/0240735 | A1 * | 8/2023 | Doyle | A61B 17/92 606/100 |
| 2024/0024012 | A1 | 1/2024 | Dittrich et al. | |

FOREIGN PATENT DOCUMENTS

| | | | |
|---|---|---|---|
| AU | 2017320580 | | 4/2023 |
| AU | 2021378282 | | 6/2023 |
| AU | 2022227599 | | 8/2023 |
| CA | 3063569 | | 11/2018 |
| CA | 3209081 | | 8/2022 |
| CA | 3211071 | | 9/2022 |
| CH | 701397 | A2 | 1/2011 |
| CN | 2423872 | Y | 3/2001 |
| CN | 204863450 | U | 12/2015 |
| CN | 109070324 | | 12/2018 |
| CN | 108602180 | | 12/2022 |
| CN | 116801840 | A | 9/2023 |
| CN | 117414174 | | 1/2024 |

(56) References Cited

FOREIGN PATENT DOCUMENTS

| | | | |
|---|---|---|---|
| DE | 102010017726 | A1 | 1/2011 |
| EP | 0290375 | A1 | 11/1988 |
| FR | 2054809 | A5 | 5/1971 |
| JP | 7127068 | | 8/2022 |
| JP | 2022166207 | | 11/2022 |
| JP | 7366968 | | 10/2023 |
| JP | 7375104 | | 10/2023 |
| JP | 7404463 | | 12/2023 |
| JP | 2023551117 | | 12/2023 |
| JP | 2024013234 | | 1/2024 |
| JP | 2024504977 | | 2/2024 |
| JP | 2024505231 | | 2/2024 |
| JP | 2024505239 | | 2/2024 |
| JP | 2024505543 | | 2/2024 |
| JP | 2024507954 | | 2/2024 |
| WO | WO-8802246 | A2 | 4/1988 |
| WO | WO-8906516 | A1 | 7/1989 |
| WO | WO-2008130904 | A2 | 10/2008 |
| WO | WO-2016112397 | A1 | 7/2016 |
| WO | WO-2018044348 | A1 | 3/2018 |
| WO | WO-2018217250 | A1 | 11/2018 |
| WO | WO-2022103835 | A1 | 5/2022 |
| WO | WO-2022159704 | A1 | 7/2022 |
| WO | WO-2022165215 | A1 | 8/2022 |
| WO | WO-2022165223 | A1 | 8/2022 |
| WO | WO-2022165357 | A1 | 8/2022 |
| WO | WO-2022182772 | A1 | 9/2022 |

OTHER PUBLICATIONS

"U.S. Appl. No. 17/587,794, Response filed Aug. 28, 2023 to Restriction Requirement mailed Jun. 27, 2023", 7 pgs.

"U.S. Appl. No. 17/587,794, Restriction Requirement mailed Jun. 27, 2023", 7 pgs.

"International Application Serial No. PCT/US2021/058776, International Preliminary Report on Patentability mailed May 25, 2023", 10 pgs.

"International Application Serial No. PCT/US2022/013312, International Preliminary Report on Patentability mailed Aug. 3, 2023", 12 pgs.

"International Application Serial No. PCT/US2022/014368, International Preliminary Report on Patentability mailed Aug. 10, 2023", 10 pgs.

"International Application Serial No. PCT/US2022/014380, International Preliminary Report on Patentability mailed Aug. 10, 2023", 9 pgs.

"International Application Serial No. PCT/US2022/014596, International Preliminary Report on Patentability mailed Aug. 10, 2023", 7 pgs.

"International Application Serial No. PCT/US2022/017537, International Preliminary Report on Patentability mailed Sep. 7, 2023", 7 pgs.

"International Application Serial No. PCT/US2021/058776, International Search Report mailed Feb. 9, 2022", 5 pgs.

"International Application Serial No. PCT/US2021/058776, Written Opinion mailed Feb. 9, 2022", 8 pgs.

"International Application Serial No. PCT/US2022/013312, International Search Report mailed Jun. 24, 2022", 6 pgs.

"International Application Serial No. PCT/US2022/013312, Invitation to Pay Additional Fees mailed May 3, 2022", 5 pgs.

"International Application Serial No. PCT/US2022/013312, Written Opinion mailed Jun. 24, 2022", 10 pgs.

"International Application Serial No. PCT/US2022/014368, International Search Report mailed May 30, 2022", 7 pgs.

"International Application Serial No. PCT/US2022/014368, Invitation to Pay Additional Fees mailed Apr. 5, 2022", 10 pgs.

"International Application Serial No. PCT/US2022/014368, Written Opinion mailed May 30, 2022", 8 pgs.

"International Application Serial No. PCT/US2022/014380, International Search Report mailed Jun. 24, 2022", 6 pgs.

"International Application Serial No. PCT/US2022/014380, Written Opinion mailed Jun. 24, 2022", 7 pgs.

"International Application Serial No. PCT/US2022/014596, International Search Report mailed May 10, 2022", 4 pgs.

"International Application Serial No. PCT/US2022/014596, Written Opinion mailed May 10, 2022", 5 pgs.

"International Application Serial No. PCT/US2022/017537, International Search Report mailed Jun. 1, 2022", 4 pgs.

"International Application Serial No. PCT/US2022/017537, Written Opinion mailed Jun. 1, 2022", 5 pgs.

Budimir, Miles, "What is a rack and roller pinion?", [Online]. Retrieved from the Internet: <https://www.motioncontroltips.com/rack-roller-pinion/>, (Nov. 10, 2017), 13 pgs.

Nexen, "Rack and Roller Pinion System", [Online]. Retrieved from the Internet: <https://www.nexengroup.com/nxn/products/prod-nav/lp/Roller+Pinion+System>, (Accessed online Apr. 27, 2021), 10 pgs.

U.S. Appl. No. 18/222,830, filed Jul. 17, 2023, Linear Electric Surgical Hammer Impact Tool.

"U.S. Appl. No. 17/587,794, Notice of Allowance mailed Nov. 15, 2023", 10 pgs.

"European Application Serial No. 23186404.2, Extended European Search Report mailed Nov. 23, 2023", 8 pgs.

"European Application Serial No. 21820393.3, Response Filed Dec. 14, 2023 to Communication pursuant to Rules 161(1) and 162 EPC mailed Jul. 6, 2023", 10 pgs.

"U.S. Appl. No. 17/678,807, Notice of Allowance mailed Feb. 14, 2024", 16 pgs.

"Australian Application Serial No. 2021378282, First Examination Report mailed Mar. 7, 2024", 3 pgs.

* cited by examiner

ORTHOPEDIC IMPACTOR TOOL

PRIORITY CLAIM

The present application claims priority to U.S. Provisional Application No. 63/143,548, entitled "Orthopedic Impactor Tool," filed on Jan. 29, 2021; the contents of which are hereby incorporated by reference in their entirety.

FIELD OF THE DISCLOSURE

The present disclosure relates generally to surgical instruments and use thereof. More specifically, the present disclosure relates to an orthopedic impactor tool and methods of use thereof.

BACKGROUND

Orthopedic surgeons commonly utilize tools for cutting or carving bone that require a hammer or mallet to transmit an impaction force to the tool. An example is a broach tool used to prepare the proximal end of a femur to receive the stein of a hip implant. Such broaches can be used with a hammer wielded by the physician or with a pneumatic "jackhammer" like tool. However, striking a broach tool with a hammer can be tiresome and can cause high stresses on the physician's own joints, such as the shoulder joint. Furthermore, pneumatic impact tools require connection to an air hose, which can be inconvenient and can potentially limit the physician's ability to orient the tool in the desired manner.

SUMMARY

The following, non-limiting examples, detail certain aspects of the present subject matter to solve the challenges and provide the benefits discussed herein, among others.

Example 1 is an orthopedic impact tool comprising: a housing including a hand grip portion and an impact mechanism housing portion; a tube assembly comprising a first tube portion and a second tube portion; a reverse impact plate disposed in between the first tube portion and the second tube portion; an anvil comprising a forward impact surface; and an impact mechanism comprising: a motor, a piston disposed within the first tube portion of the tube assembly, a rotary to linear conversion mechanism drivingly connecting the motor to the piston, a ram disposed in the second tube portion and movable into contact between the reverse impact plate and the forward impact surface.

In Example 2, the subject matter of Example 1 optionally includes wherein the tube assembly, the anvil, and the reverse impact plate are axially shiftable rearward from a neutral position within the housing for activating a forward impact cycle.

In Example 3, the subject matter of any one or more of Examples 1-2 optionally include wherein the tube assembly, the anvil, and the reverse impact plate are axially shiftable forward from a neutral position within the housing for activating a rearward impact cycle.

In Example 4, the subject matter of any one or more of Examples 1-3 optionally include wherein the tube assembly defines a chamber port that is: open to an atmosphere when the tube assembly is in a neutral position; and closed to the atmosphere when the tube assembly is shifted rearward from the neutral position.

In Example 5, the subject matter of any one or more of Examples 1-4 optionally include wherein forward shifting of the tube assembly and the anvil prevents the ram from contacting the forward impact surface of the anvil during a rearward impact cycle.

In Example 6, the subject matter of any one or more of Examples 1-5 optionally include wherein rearward shifting of the tube assembly and the reverse impact plate prevents the ram from contacting the reverse impact plate during a forward impact cycle.

In Example 7, the subject matter of any one or more of Examples 1-6 optionally include wherein the rotary to linear conversion mechanism includes a swashplate.

In Example 8, the subject matter of any one or more of Examples 1-7 optionally include a three position trigger switch including an off position, a single operation position, and a continuous operation position.

In Example 9, the subject matter of any one or more of Examples 1-8 optionally include a three position trigger switch including a single operation position and a continuous operation position defined by at least one detest of the three position trigger switch.

In Example 10, the subject matter of any one or more of Examples 1-9 optionally include an energy level switch; and a control unit operative to control the motor based upon a position of the energy level switch.

In Example 11, the subject matter of any one or more of Examples 1-10 optionally include a chuck connected to the anvil.

In Example 12, the subject matter of any one or more of Examples 1-11 optionally include a frame structure disposed within the housing and supporting the tube assembly.

In Example 13, the subject matter of Example 12 optionally includes a swashplate supported by the frame structure.

Example 14 is an orthopedic impact tool comprising: a housing comprising a hand grip portion; a motor disposed in the housing; an anvil comprising an impact surface; an impact mechanism driven by the motor for providing an impact to the impact surface; a control unit in electrical communication with the motor; and a three position trigger switch in electrical communication with the control unit and including an off position, a single operation position, and a continuous operation position, wherein when the three position trigger switch is in the single operation position, the controller is operative to control the motor to deliver a single impact to the impact surface, and wherein when the three position trigger switch is in the continuous operation position, the controller is operative to control the motor to deliver continuous impacts to the impact surface.

In Example 15, the subject matter of Example 14 optionally includes wherein the impact mechanism comprises: a tube assembly; a rotary linear conversion mechanism; and a piston disposed in the tube assembly and operatively coupled to the motor and the rotary to linear conversion mechanism.

In Example 16, the subject matter of Example 15 optionally includes wherein the tube assembly comprises a first tube portion and a second tube portion, the piston disposed within the first tube portion.

In Example 17, the subject matter of any one or more of Examples 15-16 optionally include a reverse impact plate disposed between the first tube portion and the second tube portion; and a ram disposed in the second tube portion and movable into contact between the reverse impact plate and the impact surface of the anvil.

Example 18 is an orthopedic impact tool comprising: a housing including a hand grip portion and an impact mechanism housing portion; a tube assembly comprising a first tube portion and a second tube portion; a reverse impact plate disposed in between the first tube portion and the second tube portion; an anvil comprising a forward impact surface; an impact mechanism comprising: a motor, a piston disposed within the first tube portion of the tube assembly, a rotary to linear conversion mechanism drivingly connecting the motor to the piston, a ram disposed in the second tube portion and movable into contact between the reverse impact plate and the forward impact surface.

In Example 19, the subject matter of Example 18 optionally includes wherein the tube assembly, the anvil, and the reverse impact plate are axially shiftable rearward from a neutral position within the housing for activating a forward impact cycle, and the tube assembly, the anvil, and the reverse impact plate are axially shiftable forward from a neutral position within the housing for activating a rearward impact cycle.

In Example 20, the subject matter of any one or more of Examples 18-19 optionally include a chuck connected to the anvil.

In Example 21, the orthopedic impact tools, systems, and/or methods of any one or any combination of Examples 1-20 can optionally be configured such that all elements or options recited are available to use or select from.

BRIEF DESCRIPTION OF THE FIGURES

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

As an alternative to a pneumatic piston driven system, disclosed herein are electrically driven systems. Specifically, the orthopedic impact tools disclosed herein can include a housing, a tube assembly, a reverse impact plate, an anvil and an impact mechanism. The housing can include a hand grip portion and an impact mechanism housing portion. The tube assembly can include a first tube portion and a second tube portion. The reverse impact plate can be disposed in between the first tube portion and the second tube portion. The anvil can include a forward impact surface. The impact mechanism can include a motor, a piston, a ram, and a rotary to linear conversion mechanism drivingly connecting the motor to the piston. The piston can be disposed within the first tube portion and the ram can be disposed in the second tube portion and movable into contact between the reverse impact plate and the forward impact surface.

The tube assembly, the anvil, and the reverse impact plate can be axially shiftable rearward from a neutral position within the housing for activating a forward impact cycle. The tube assembly, the anvil, and the reverse impact plate can be axially shiftable forward from the neutral position within the housing for activating a rearward impact cycle.

As part of developing a reciprocating motion, the tube assembly can define a chamber port that is open to an atmosphere when the tube assembly is in a neutral position and closed to the atmosphere when the tube assembly is shifted rearward from the neutral position. During motion, air can be drawn into the tube assembly to create pressure used to drive elements, such as the ram, the generate impact forces.

The orthopedic impact tools can be controlled by an energy level switch and a three position trigger switch. A control unit can be operative to control the motor based upon a position of the energy level switch to change a magnitude of impact forces delivered. The three position trigger switch can include an off position, a single operation position, and a continuous operation position. When in the single operation position the orthopedic impact tools can deliver a single impact. When in the continuous position, the orthopedic impact tools can deliver continuous impacts.

The above discussion is intended to provide an overview of subject matter of the present patent application. It is not intended to provide an exclusive or exhaustive explanation of the invention. The description below is included to provide further information about the present patent application.

Figure 1:
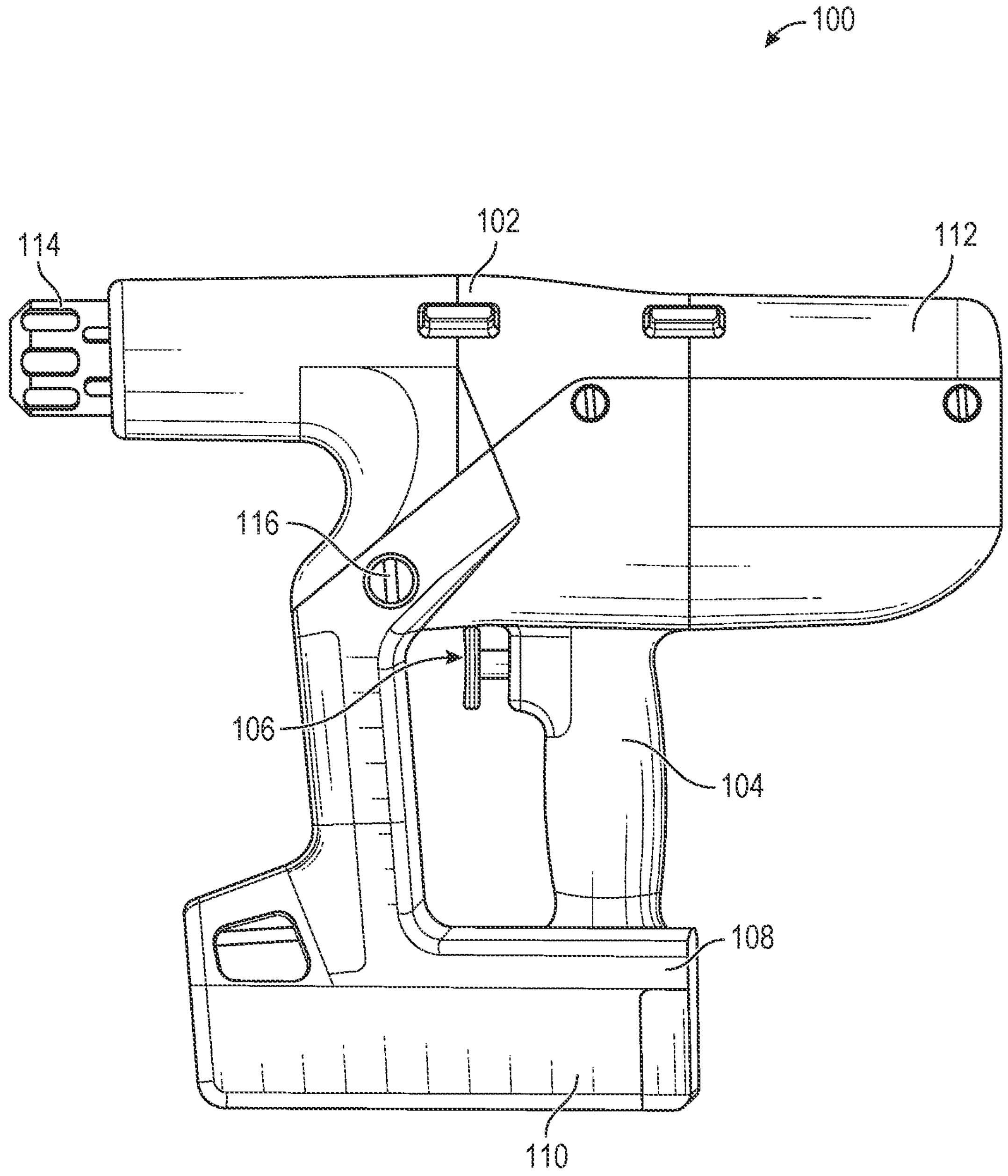
FIG. 1 shows a side plan view of an orthopedic impact tool consistent with at least one example of this disclosure.

Turning now to the figures, FIG. 1 shows an orthopedic impactor tool 100 consistent with at least one example of this disclosure. The orthopedic impactor tool 100 can include a housing 102 that can define a hand grip portion 104. The hand grip portion 104 can include a trigger 106, a battery support portion 108 that can support a battery pack 110 and an impact mechanism housing portion 112. The impact mechanism housing portion 112 can support an impact mechanism 228 therein that can deliver impacts to a chuck 114.

Figure 2:
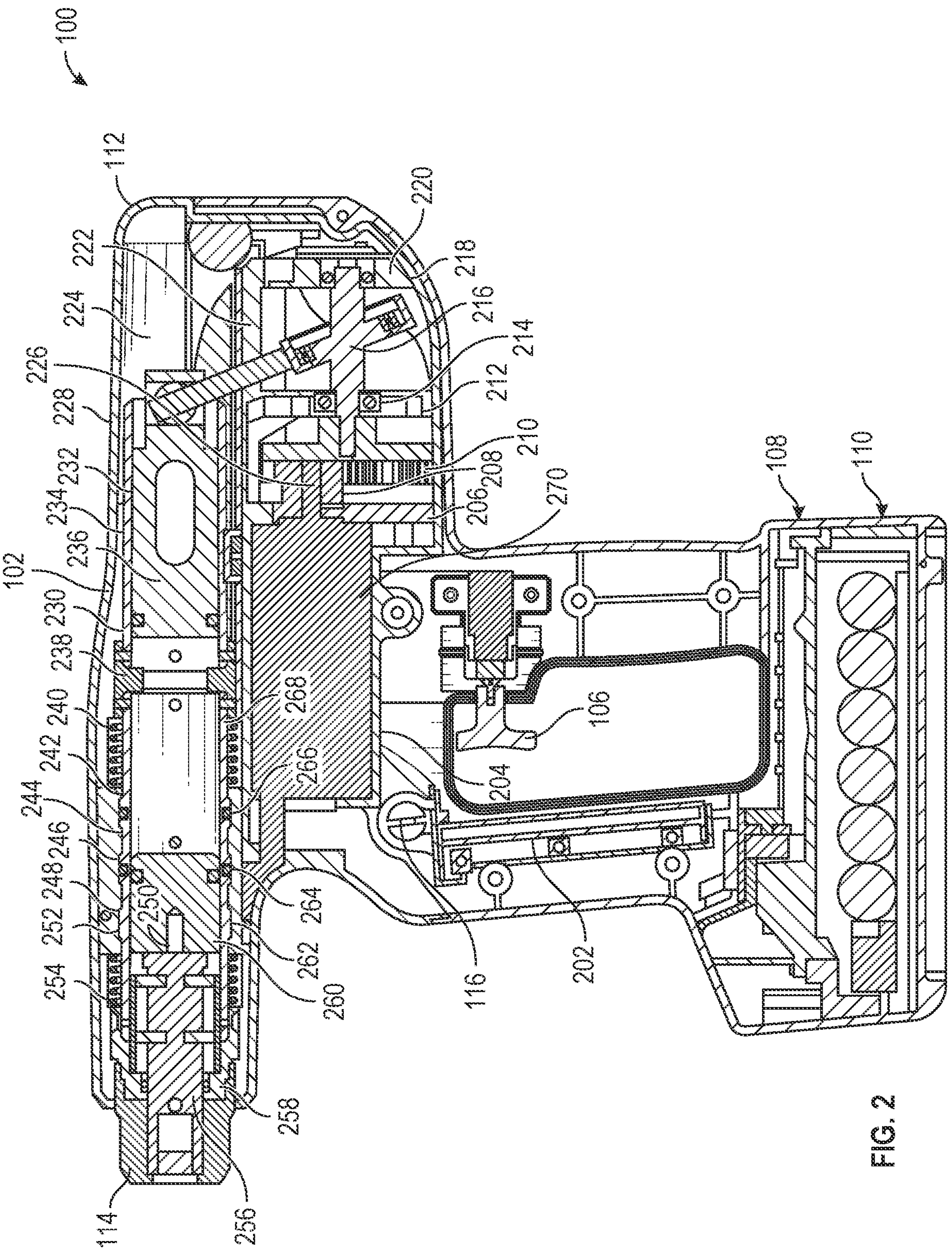
FIG. 2 shows a cross-sectional view of an orthopedic impact tool consistent with at least one example of this disclosure.

With reference to FIG. 2, a sectional view of the orthopedic impactor tool 100 is shown including details of the impact mechanism 228 disposed within the impact mechanism housing portion 112. As shown in FIG. 2, the impact mechanism 228 can include a motor 270 that can include a drive shaft 226. The drive shaft 226 can be connected to a drive gear 208. The drive gear 208 can be engaged with a driven gear wheel 210 that can have internal gear teeth. The driven gear wheel 210 can be connected to a swashplate 216 or other rotary to linear conversion device. For example, the swashplate 216 can be a crank arm. The swashplate 216 or other rotary to linear conversion device can be connected to a piston 236 that can be disposed within a rear portion 232 of a tube assembly 40. The tube assembly 230 can include a forward portion 268 that can be separated from the rear portion 232 by a reverse impact plate 238.

A ram 260 can be disposed in the forward portion 268 of the tube assembly 230 and can be movable between a forward position for impacting a forward impact surface 250 of an anvil 256 and a rearward position for impacting the reverse impact plate 238. The chuck 114 can be connected to a forward end of the anvil 256. The chuck 114 can be adapted to engage a broach or other tool (not shown) that can be utilized for creating a cavity within a bone for receiving a prosthetic device. When the ram 260 contacts the impact surface 250 of the anvil 256, impact energy can be transferred through the proximal impact surface 250 to the implement. When the ram 260 contacts the reverse impact plate 238, impact energy can be transferred through the tube assembly 230 and the chuck 114 to the implement.

The housing 102 can define a hollow cavity 224 including an integrally formed internal wall structure 204 that can support the motor 270, the trigger 106 and a controller unit 202. A frame 222 can be further received within the cavity 224 and can include a first support portion 206 for supporting the drive shaft 226 and second and third support portions 212 and 218 for supporting forward and rearward swashplate support, bearings 214 and 220.

The frame 222 can further include a first tube assembly support portion 234 that can support the rear portion 232 of the tube assembly 230. The frame 222 can also include a second tube assembly support portion 246 that can support the forward portion 268 of the tube assembly 230. The tube assembly can slide within the housing 102 and can be guided by the first tube assembly support portion 234 and the second tube assembly support portion 246. The second tube assembly support portion 246 can further include a plurality of annular grooves 262, 264, and 266 disposed in an inner surface and defined by a plurality of land portions 242, 244, 248, and 252.

A first spring 254 can be disposed between a forward end of the tube assembly support portion 246 of the frame 222 and a nose cap 258 of the forward portion 268 of the tube assembly 230. A second spring 240 can be disposed between a rear end of the tube assembly support portion 246 of the frame 222 and an outer annular body 902 of the reverse impact plate 238.

Figure 4:
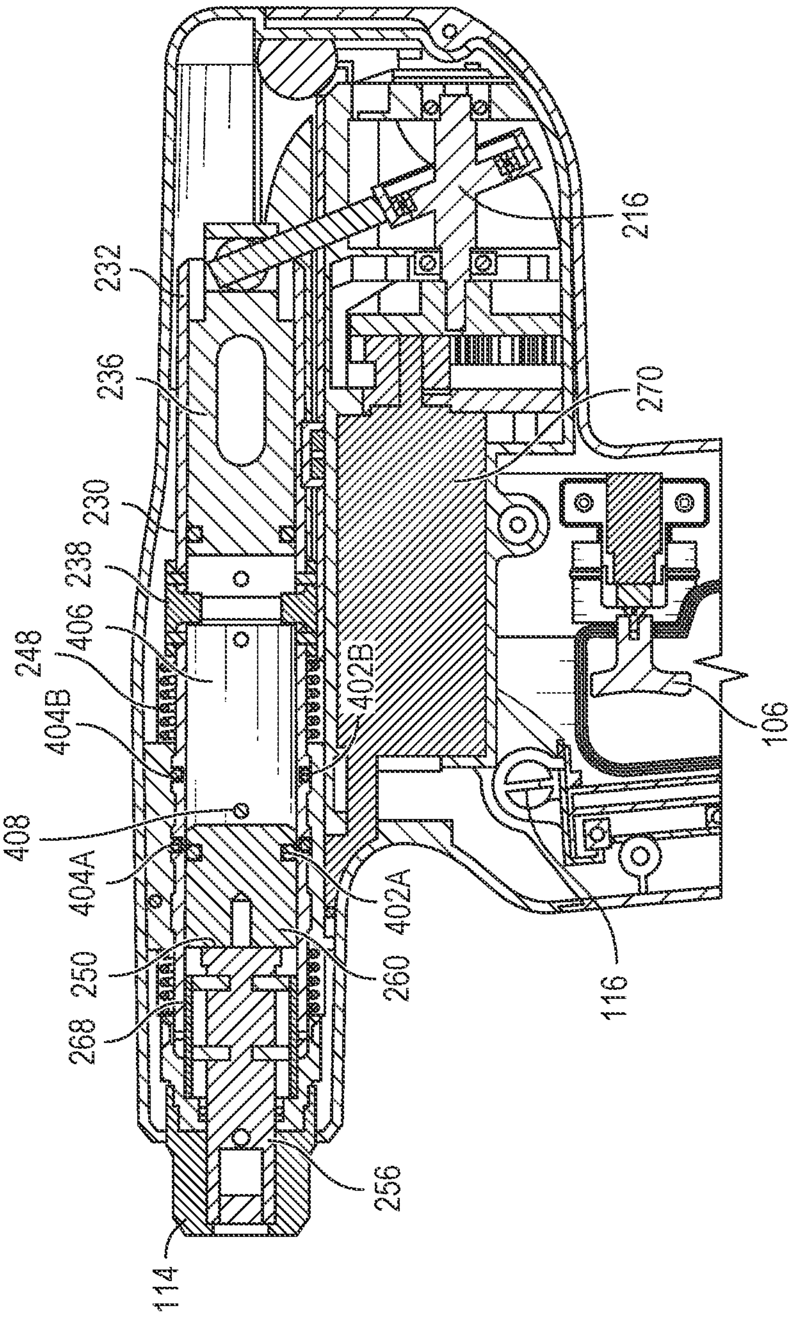
FIG. 4 shows a cross-sectional view of an impact mechanism of an orthopedic impact tool consistent with at least one example of this disclosure.

With reference to FIG. 4, the forward portion 268 of the tube assembly 230 can include a pair of recessed grooves 404 (labeled individually as grooves 404A and 404B) each supporting an O-ring 402A and 402B therein. As shown in FIG. 4, the forward portion 268 of the tube assembly 230 can include a chamber 406 defining a chamber port 408 that can be in communication with the atmosphere when in a neutral state or closed off from the atmosphere during forward and reverse impact operations, as disclosed herein.

Figure 3A:
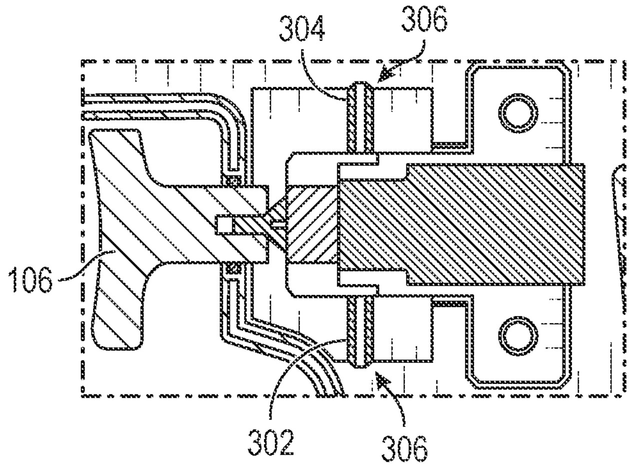
FIGS. 3A, 3B, and 3C shows plan views of a three position trigger consistent with at least one example of this disclosure.
Figure 3B:
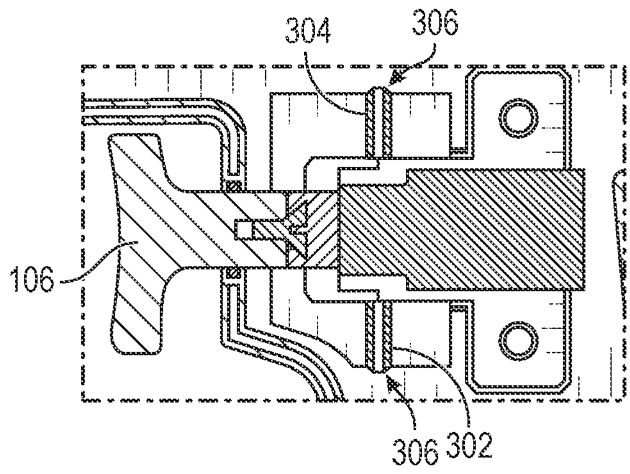
Figure 3C:
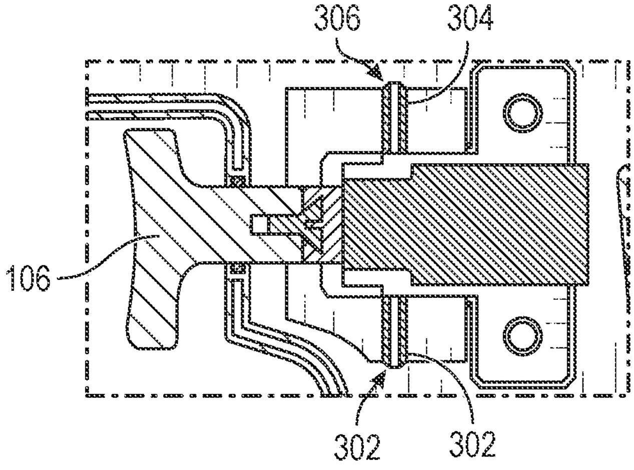

As shown in FIGS. 3A, 3B, and 3C, the trigger 106 can have an off position (FIG. 3A) and can be depressed to two different depths. In a first depressed position, as shown in FIG. 3B, two spring pins 304 can reach a pair of detents at 306. In a second further depressed position, the spring pins 304 move past the detents at 306. Depressing the trigger 106 to the first depth can cause a single impact of the impact mechanism 228 to be delivered. Further depressing the trigger 106 to the second depth can cause impacts of the impact mechanism 228 to be delivered continuously until the trigger 106 is released.

The tool 100 can further include an impact energy switch 116. The impact energy switch 116 can be a rotary switch that can provide an input to the controller unit 202. In the first position of the impact energy switch 116, the controller unit 202 can cause the impact mechanism 228 to deliver low-energy impacts. In the second position of the impact energy switch 116, the controller unit 202 can cause the impact mechanism 228 to deliver high-energy impacts as disclosed herein.

The chuck 114, the anvil 256, the reverse impact plate 238, the ram 260 and the tube assembly 230 can be "shifting components" that can translate with respect to the rest of the tool 100 along the axis of the tube assembly 230. With reference to FIG. 4, a cross sectional view of the orthopedic impact tool 100 is shown in a neutral state. In the neutral state, the ram 260 and piston 236 are in a forward position. In addition, the tube assembly 230 is positioned by the first and second springs 254, 240 such that the chamber port 406 is open to the atmosphere so movement of the piston 236 does not create compression within the tube assembly 230.

Figure 5:
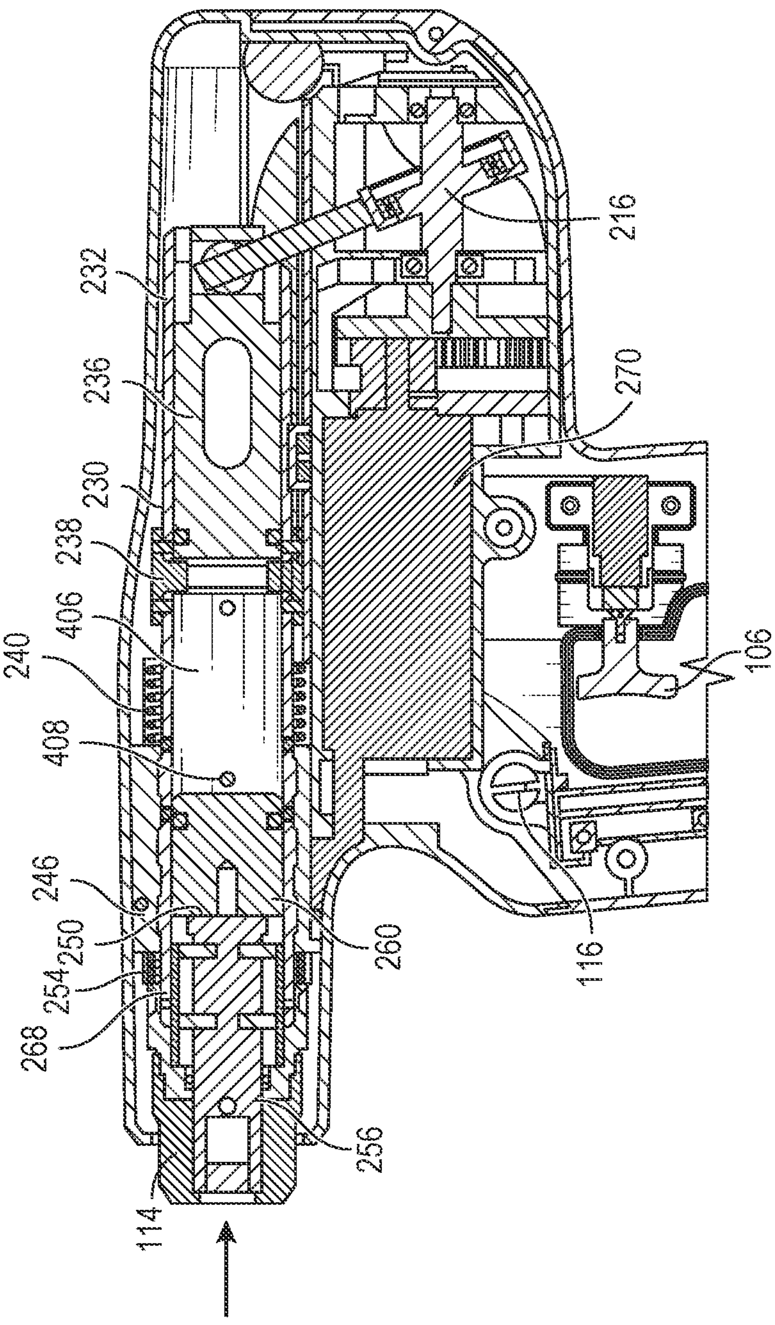
FIG. 5 shows a cross-sectional view of an impact mechanism of an orthopedic impact tool consistent with art least one example of this disclosure.

In order to activate a forward impact cycle, an implement held by the chuck 114 of the orthopedic tool 100 can be pressed against a bone and the shifting components 114, 230, 238, 260, 256 can be pressed rearward so that the spring 254 is in a compressed state, as shown in FIG. 5, so that the chamber port 406 is sealed and the pressure chamber 302 is closed. In particular, the O-rings 402A and 402B can sealingly engage the lands 244, 242 on opposite sides of groove 266, closing off the port 406 from atmosphere. The closing of the pressure chamber 302 allows high and low pressures to form within the tube assembly 230 so that reciprocal movement of the piston 236 can cause the ram 260 to reciprocate and contact the impact surface 250 of the anvil 256.

Figure 6:
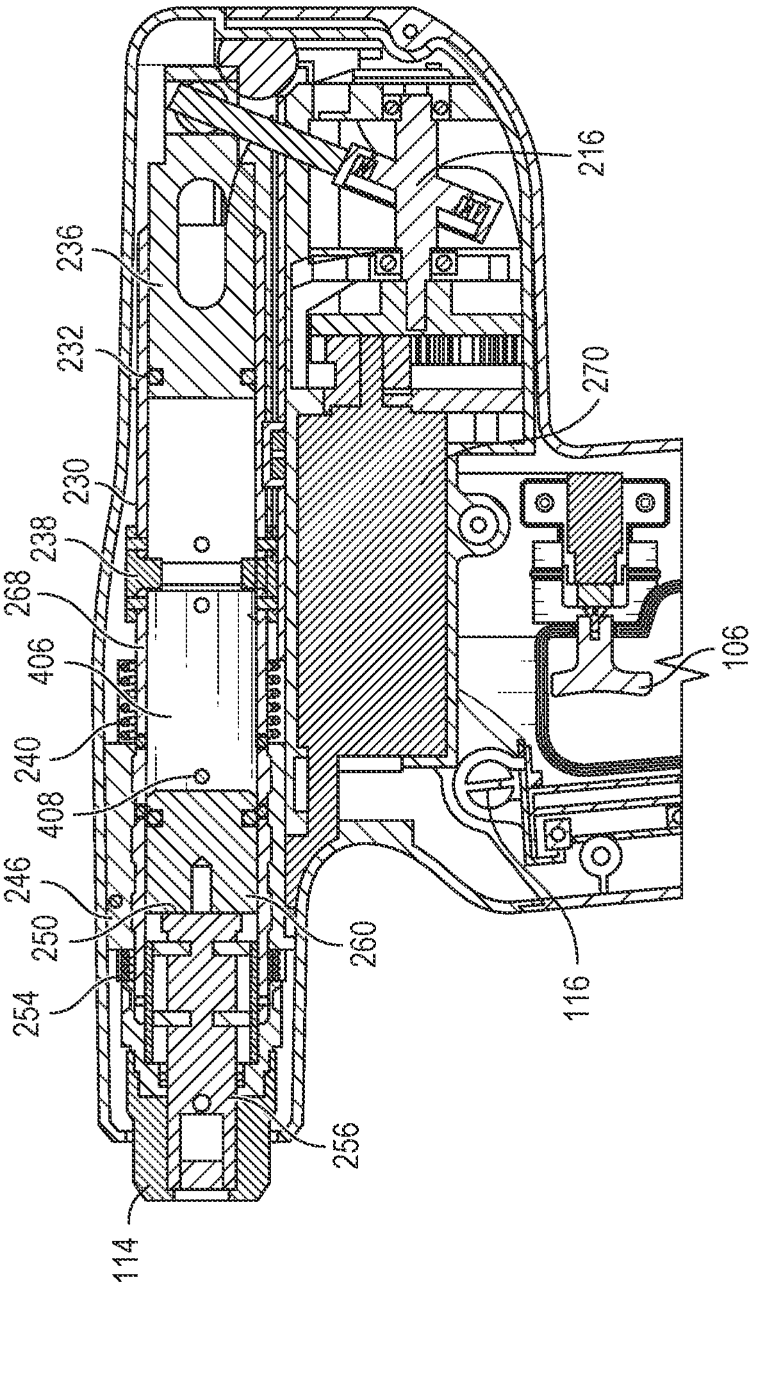
FIG. 6 shows a cross-sectional view of an impact mechanism of an orthopedic impact tool shown consistent with at least one example of this disclosure.
Figure 7:
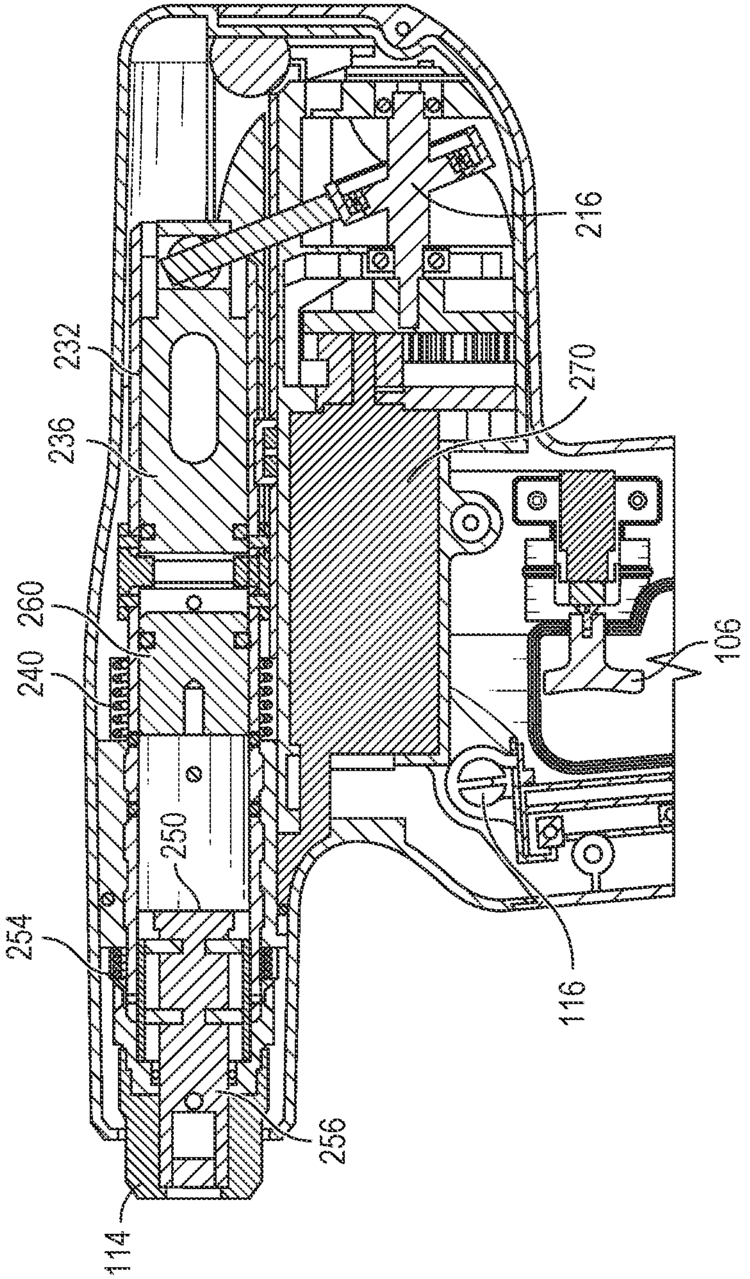
FIG. 7 shows a cross-sectional view of an impact mechanism of an orthopedic impact tool consistent with at least one example of this disclosure.

To begin, the controller unit 202 can respond to the activation of the trigger 106 to instruct the motor 270 to begin rotating. The motor 270 can turn the gears 208, 210 and can rotate the swashplate 216 as well. The rotation of the swashplate 216 can cause it to pull the piston 236 rearward, as shown in FIG. 6. This can create a low pressure region in the pressure chamber 302 that can draw the ram 260 rearward. The motor 270 and swashplate 216 can continue to rotate, causing the piston 236 to be moved forward. This can create a high pressure region in the pressure chamber 302 as shown in FIG. 7.

Figure 8:
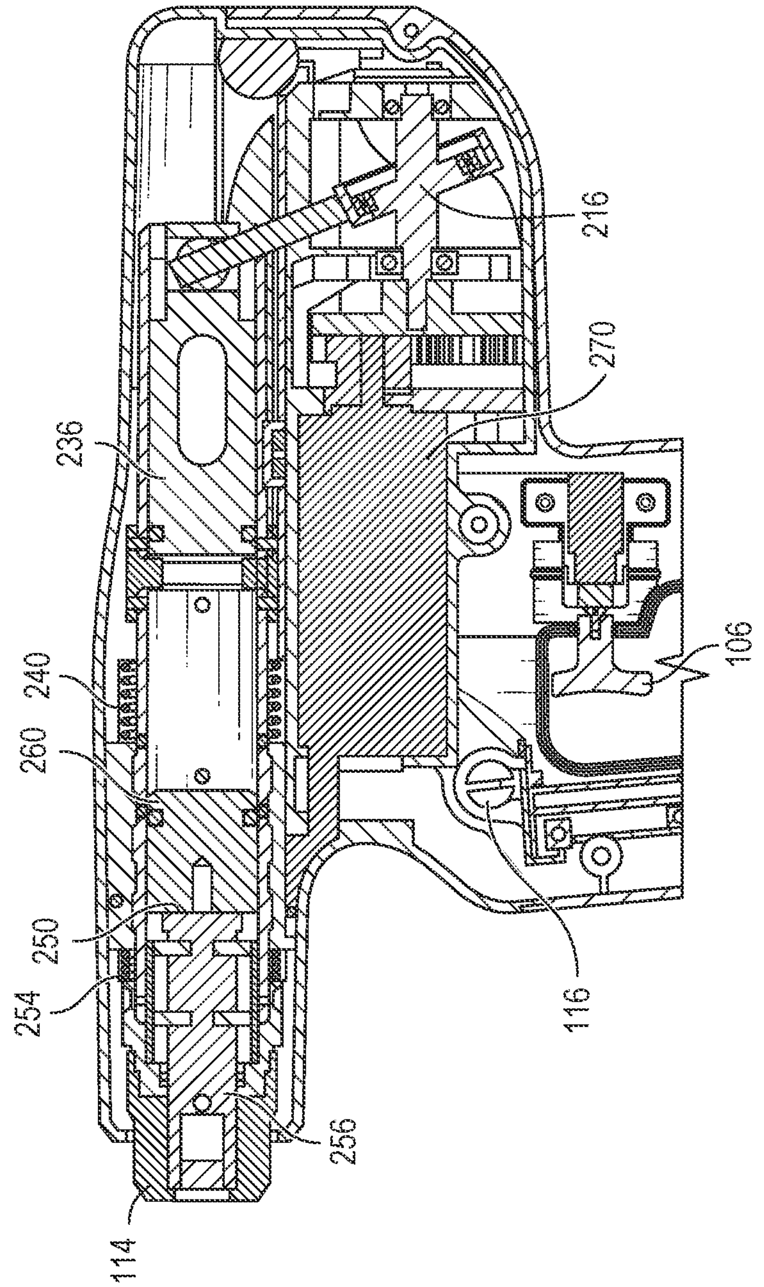
FIG. 8 shows a cross-sectional view of an impact mechanism of an orthopedic impact tool consistent with at least one example of this disclosure.

The high pressure region can push the rain 260 proximally until it contacts the forward impact surface 250 of the anvil 256, as shown in FIG. 8. The kinetic energy of the ram 260 can be transferred through the anvil 256 to the orthopedic implement. The rearward shifting of the shifting components 114, 230, 238, 260, 256 can prevent the ram 260 from contacting the rearward impact plate 238 during the forward impact cycle.

The speed at which the motor 270 and swashplate 216 rotate can determine the impact energy of the ram 260 and the frequency of the impacts. The speed can be modified by the controller unit 202 when the impact energy switch 116 is rotated.

Figure 9:
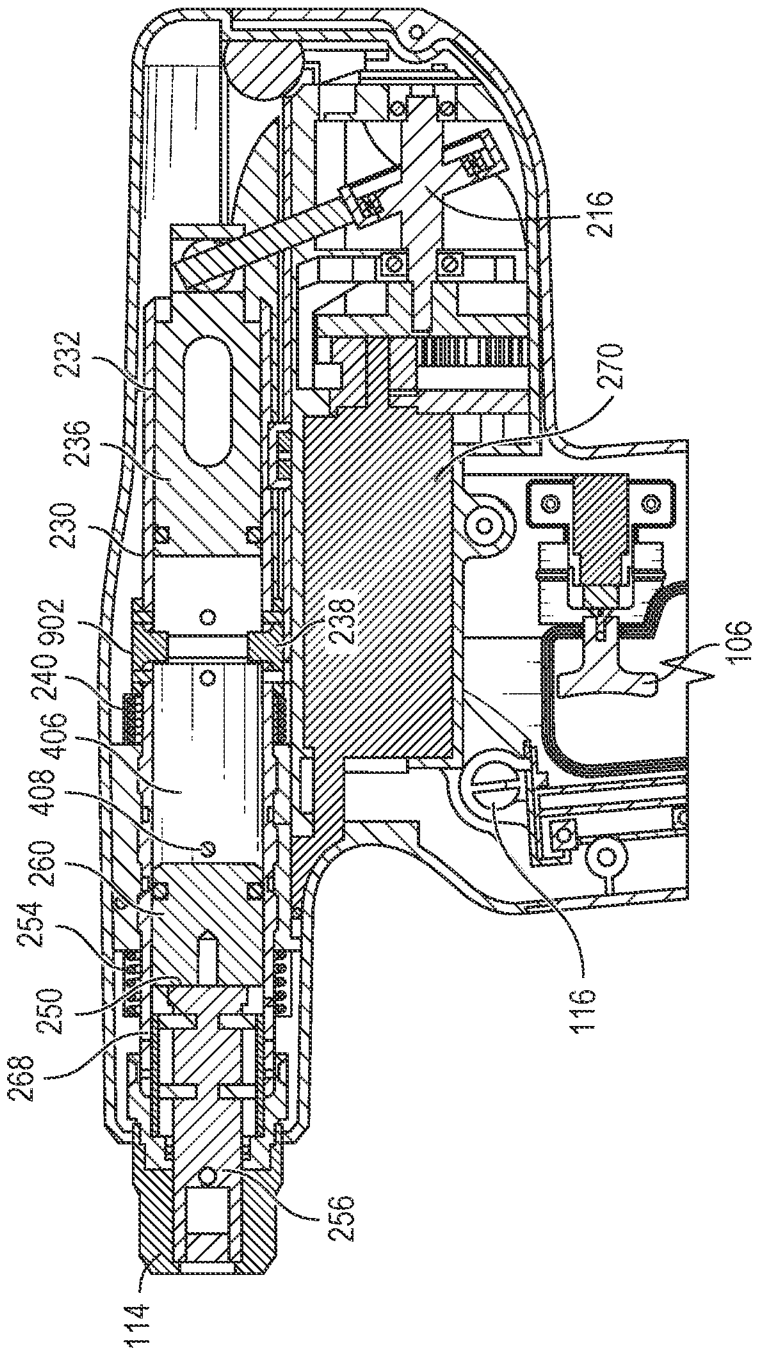
FIG. 9 shows a cross-sectional view of an impact mechanism of an orthopedic impact tool consistent with at least one example of this disclosure.

In order to activate a rearward impact cycle, the device can start in a neutral state, as shown in FIG. 4, where again, the pressure chamber 302 is open to atmosphere via the chamber port 406. Before impacting, an external pulling force can be applied to the orthopedic impact tool 100 to compress the spring 240 putting the device in an extended state as shown in FIG. 9. In the extended state as shown in FIG. 9, the shifting components 114, 230, 238, 260, 256 can be pulled forward so that the chamber port 406 can be sealed off and the pressure chamber 302 can be closed to allow high and low pressures to form within the pressure chamber 302. Sealing of the chamber port 406 can occur when the O-rings 402A and 402B engage the lands 248, 244 and closes off the groove 264 from atmosphere.

Figure 10:
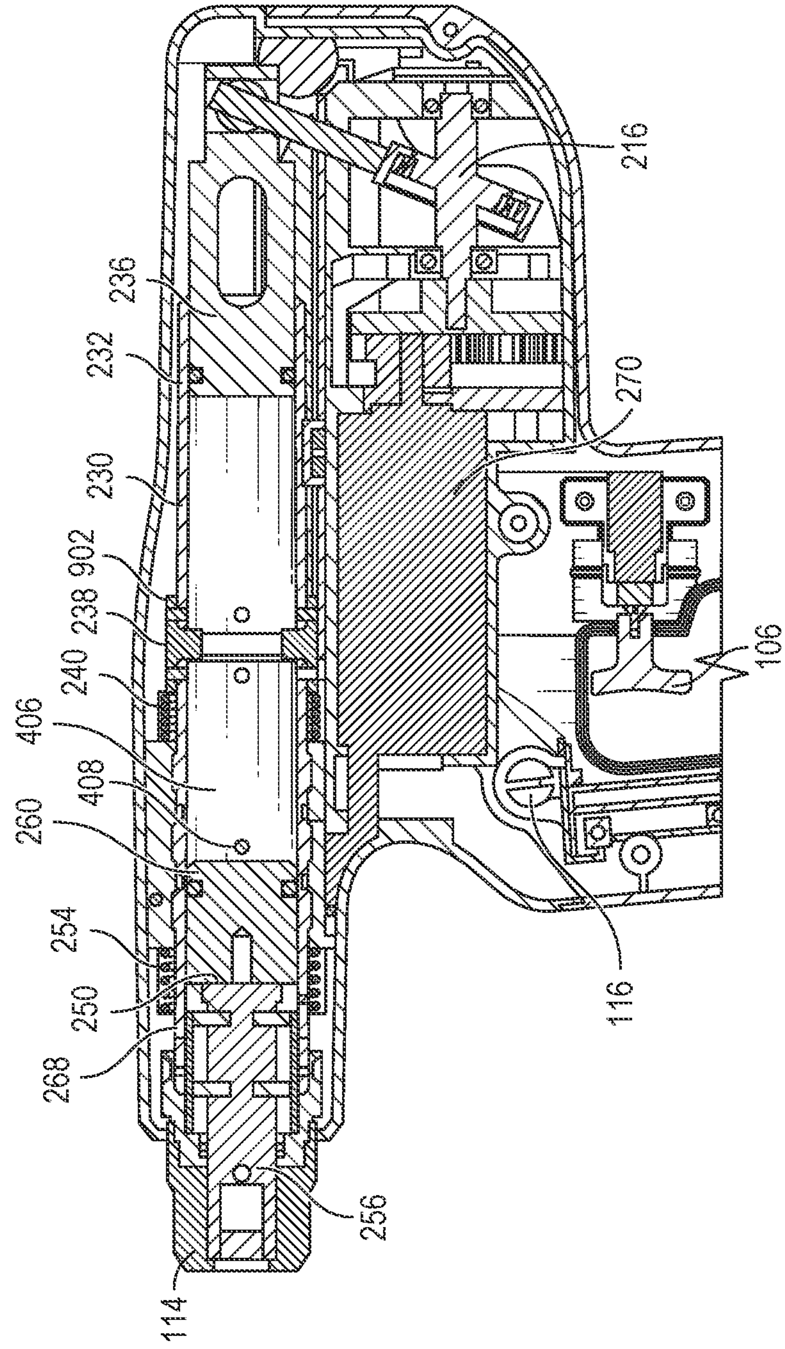
FIG. 10 shows a cross-sectional view of an impact mechanism of an orthopedic impact tool consistent with at least one example of this disclosure.
Figure 11:
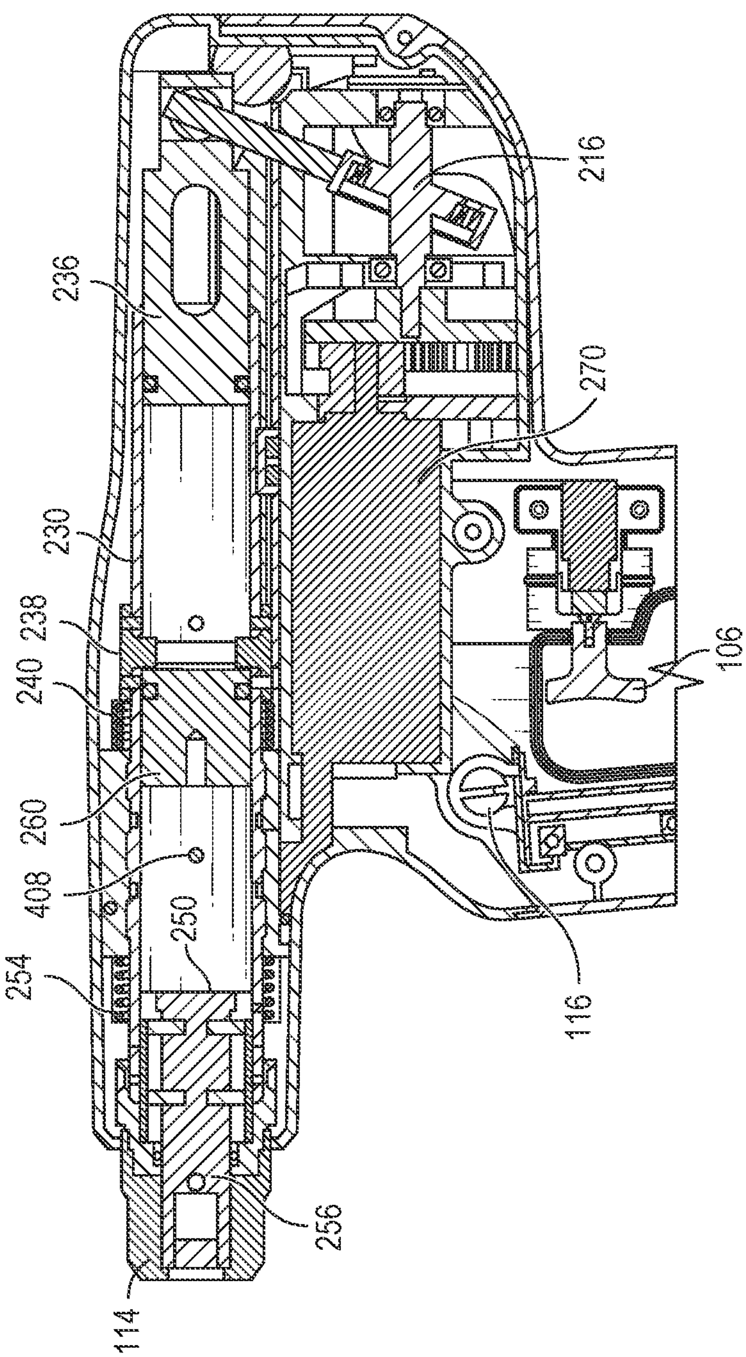
FIG. 11 shows a cross-sectional view of an impact mechanism of an orthopedic impact tool consistent with at least one example of this disclosure.

To begin the rearward impact cycle, the controller unit 202 can respond to the depression of the trigger 106 and instruct the motor 270 to begin rotating (e.g., by transmitting a signal, such as a voltage, to the motor 270). The motor 270 can turn the gears 208, 210 and rotate the swashplate 216 as well. The rotation of the swashplate 216 can cause it to pull the piston 236 rearward, as shown in FIG. 10. This can create a low pressure region in the pressure chamber 302 that can draw the ram 260 rearward. The low pressure region can pull the ram 260 rearwardly until it contacts the reverse impact plate 238, as shown in FIG. 11. The kinetic energy of the ram 260 can then be transferred through the rearward impact plate 238, the tribe assembly 230, and the chuck 114 to the orthopedic implement.

Figure 12:
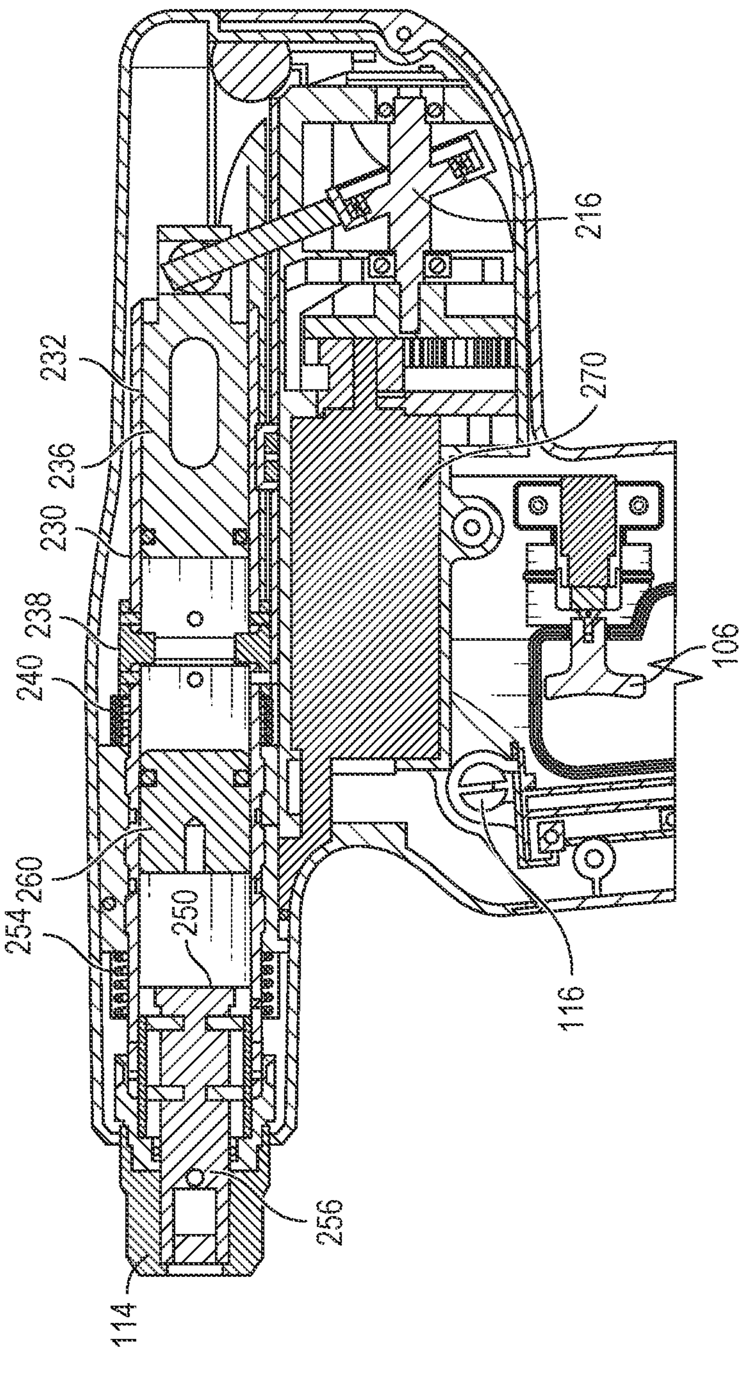
FIG. 12 shows a cross-sectional view of an impact mechanism of an orthopedic impact tool consistent with at least one example of this disclosure.

The motor 270 and swashplate 216 can continue to rotate, causing the piston 236 to be moved forward. This can create a high pressure region in the pressure chamber 302 as shown in FIG. 12. The high pressure region can push the ram 260 forward within the tube assembly 230. The forward shifting of the shifting components 114, 230, 238, 260, 256 can prevent the ram 260 from contacting the forward impact surface 250 of the anvil 256 during the rearward impact cycle.

The orthopedic impact tool 100 of the present disclosure can be prevented from delivering impacts when the orthopedic impact tool 100 is in the neutral position. The orthopedic impact tool 100 can only operate when the orthopedic impact tool 100 is being pushed forward toward a bone or pulled rearward away from the bone to provide a simple transition between delivering forward or rearward impacts. The orthopedic impact tool 100 can also provide for multiple impact level choices. The tool can also use a three position trigger switch to switch between single impact and continuous impact mode. The three position trigger switch can allow for more reliable control than a duration system.

Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more," In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An orthopedic impact tool comprising:

a housing including a hand grip portion and an impact mechanism housing portion;

a tube assembly comprising a first tube portion and a second tube portion;

a reverse impact plate disposed in between the first tube portion and the second tube portion;

an anvil comprising a forward impact surface, wherein the tube assembly, the anvil, and the reverse impact plate are axially shiftable rearward from a neutral position within the housing for activating a forward impact cycle; and an impact mechanism comprising:

a motor, a piston disposed within the first tube portion of the tube assembly, a rotary to linear conversion mechanism drivingly connecting the motor to the piston, a ram disposed in the second tube portion and movable into contact between the reverse impact plate and the forward impact surface.

2. The impact tool of claim 1, wherein the tube assembly, the anvil, and the reverse impact plate are axially shiftable forward from a neutral position within the housing for activating a rearward impact cycle.

3. The orthopedic impact tool of claim 1, wherein the tube assembly defines a chamber port that is:

open to an atmosphere when the tube assembly is in a neutral position; and closed to the atmosphere when the tube assembly is shifted rearward from the neutral position.

4. The orthopedic impact tool of claim 1, wherein forward shifting of the tube assembly and the anvil prevents the ram from contacting the forward impact surface of the anvil during a rearward impact cycle.

5. The orthopedic impact tool of claim 1, wherein rearward shifting of the tube assembly and the reverse impact plate prevents the ram from contacting the reverse impact plate during a forward impact cycle.

6. The orthopedic impact tool of claim 1, wherein the rotary to linear conversion mechanism includes a swashplate.

7. The orthopedic impact tool of claim 1, further comprising a three position trigger switch including an off position, a single operation position, and a continuous operation position.

8. The orthopedic impact tool of claim 1, further comprising a three position trigger switch including a single operation position and a continuous operation position defined by at least one detent of the three position trigger switch.

9. The orthopedic impact tool of claim 1, further comprising:

an energy level switch; and a control unit operative to control the motor based upon a position of the energy level switch.

10. The orthopedic impact tool of claim 1, further comprising a chuck connected to the anvil.

11. The orthopedic impact tool of claim 1, further comprising a frame structure disposed within the housing and supporting the tube assembly.

12. The orthopedic impact tool according to claim 11, further comprising a swashplate supported by the frame structure.

13. An orthopedic impact tool comprising:

a housing comprising a hand grip portion;

a motor disposed in the housing;

a tube assembly comprising a first tube portion and a second tube portion;

a reverse impact plate disposed in between the first tube portion and the second tube portion;

an anvil comprising an impact surface, wherein the tube assembly, the anvil, and the reverse impact plate are axially shiftable rearward from a neutral position within the housing for activating a forward impact cycle;

an impact mechanism driven by the motor for providing an impact to the impact surface;

a control unit in electrical communication with the motor; and a three position trigger switch in electrical communication with the control unit and including an off position, a single operation position, and a continuous operation position, wherein when the three position trigger switch is in the single operation position, the controller is operative to control the motor to deliver a single impact to the impact surface, and wherein when the three position trigger switch is in the continuous operation position, the controller is operative to control the motor to deliver continuous impacts to the impact surface.

14. The orthopedic impact tool according to claim 13, wherein the impact mechanism comprises:

a tube assembly;

a rotary to linear conversion mechanism; and a piston disposed in the tube assembly and operatively coupled to the motor and the rotary to linear conversion mechanism.

15. The orthopedic impact tool according to claim 14, wherein the tube assembly comprises a first tube portion and a second tube portion, the piston disposed within the first tube portion.

16. The orthopedic impact tool of claim 14, further comprising:

a reverse impact plate disposed between the first tube portion and the second tube portion; and a ram disposed in the second tube portion and movable into contact between the reverse impact plate and the impact surface of the anvil.

17. An orthopedic impact tool comprising:

a housing including a hand grip portion and an impact mechanism housing portion;

a tube assembly comprising a first tube portion and a second tube portion;

a reverse impact plate disposed in between the first tube portion and the second tube portion;

an anvil comprising a forward impact surface, wherein the tube assembly, the anvil, and the reverse impact plate are axially shiftable rearward from a neutral position within the housing for activating a forward impact cycle, and the tube assembly, the anvil, and the reverse impact plate are axially shiftable forward from a neutral position within the housing for activating a rearward impact cycle;

an impact mechanism comprising:

a motor, a piston disposed within the first tube portion of the tube assembly, a rotary to linear conversion mechanism drivingly connecting the motor to the piston, a ram disposed in the second tube portion and movable into contact between the reverse impact plate and the forward impact surface;

a control unit in electrical communication with the motor;

an energy level switch in electrical communication with the control unit;

a three position trigger switch in electrical communication with the control unit and including an off position, a single operation position, and a continuous operation position, wherein when the three position trigger switch is in the single operation position, the controller is operative to control the motor to deliver a single impact to the impact surface, wherein when the three position trigger switch is in the continuous operation position, the controller is operative to control the motor to deliver continuous impacts to the impact surface, and wherein the controller is operative to control the motor to deliver different impact forces based on a position of the energy level switch.

18. The orthopedic impact tool of claim 17, further comprising a chuck connected to the anvil.

* * * * *